United States Patent
Antonini et al.

(10) Patent No.: US 9,689,882 B2
(45) Date of Patent: Jun. 27, 2017

(54) AREA MONITORING SYSTEM AND CORRESPONDING METHOD FOR OPERATING THE SAME

(75) Inventors: Roberto Antonini, Turin (IT); Gian Piero Fici, Turin (IT); Marco Gaspardone, Turin (IT)

(73) Assignee: TELECOM ITALIA S.p.A., Milan (IT)

( * ) Notice: Subject to any disclaimer, the term of this patent is extended or adjusted under 35 U.S.C. 154(b) by 828 days.

(21) Appl. No.: 14/112,169

(22) PCT Filed: Apr. 27, 2011

(86) PCT No.: PCT/EP2011/056669
§ 371 (c)(1),
(2), (4) Date: Oct. 16, 2013

(87) PCT Pub. No.: WO2012/146279
PCT Pub. Date: Nov. 1, 2012

(65) Prior Publication Data
US 2014/0039825 A1  Feb. 6, 2014

(51) Int. Cl.
*G01N 35/00* (2006.01)
*G08B 21/12* (2006.01)

(52) U.S. Cl.
CPC ......... *G01N 35/0099* (2013.01); *G08B 21/12* (2013.01)

(58) Field of Classification Search
USPC ....................................................... 702/121
See application file for complete search history.

(56) References Cited

U.S. PATENT DOCUMENTS

| 2004/0012491 A1 | 1/2004 | Kulesz et al. |
| 2004/0015336 A1 | 1/2004 | Kulesz et al. |
| 2009/0273479 A1 | 11/2009 | Waugh |

FOREIGN PATENT DOCUMENTS

DE    42 28 539    3/1994

OTHER PUBLICATIONS

Anthony LaMarca in Making Sensor Networks Practical with Robots describes, printed on 2002, pp. 16.*

(Continued)

*Primary Examiner* — Tung Lau
(74) *Attorney, Agent, or Firm* — Oblon, McClelland, Maier & Neustadt, L.L.P.

(57) ABSTRACT

A monitoring system monitoring an environmental condition of an area by measuring an environmental quantity, including: a static monitoring section including plural static sensor units each configured to collect first measure data relating to the environmental quantity in respective portions of the area; a mobile monitoring section including at least one robot configured to move within the area to collect second measure data relating to the environmental quantity in a portion of the area surrounding the robot; and a central unit communicating with the static sensor units and robot to perform: conditioned to assessing an anomalous environmental condition from first measure data collected by at least one static sensor unit, commanding the robot to operate according to anomaly routines, and conditioned to assessing an anomalous environmental condition from second measure data collected by the robot, commanding at least one static sensor unit to operate according to anomaly routines.

10 Claims, 3 Drawing Sheets

(56) References Cited

OTHER PUBLICATIONS

Mohd Fauzi Othman in Wireless Sensor Network Applications: A Study in Environment Monitoring System, 2012, 7 pages.*
U.S. Appl. No. 14/359,162, filed May 19, 2014, Antonini, et al.
International Search Report Issued Sep. 23, 2011 in PCT/EP11/056669 Filed Apr. 27, 2011.

* cited by examiner

AREA MONITORING SYSTEM AND CORRESPONDING METHOD FOR OPERATING THE SAME

BACKGROUND OF THE INVENTION

The present invention relates to the field of the automated systems for monitoring areas.

DESCRIPTION OF THE RELATED ART

Nowadays, the so called Internet of Things is one of the most interesting and promising subjects in the computing and telecommunications fields. With the term of "Internet of Things", it is generally intended a networked interconnection of machines capable of making available resources that can be remotely accessed. The "machines" may be sensors, actuators, or everyday objects (such as household appliances, clothes, cars, etc.), all provided with a wired or wireless network communication capability. The "resources" may be readings of monitored parameters (e.g., readings from electricity meters, gas meters, water meters, or weather reports, traffic information, etc.), status of sensors (e.g., proximity sensors, industrial process sensors, sensors for monitoring people and patients, etc.), actuation capabilities (e.g., opening a door, triggering a process, activating an action, etc.).

On this regard, exploiting the capabilities of the modern technologies, it is possible to implement a series of advantageous services, such as for example a service for monitoring old people, an integrated service for controlling the traffic, a service for the remote inspection of an area requiring a particular degree of surveillance, a service for remotely monitoring environmental conditions of an area, and so on.

A possible known system implementing an area monitoring service provides for the use of a so-called Sensor Network (SN). Specifically, a SN consists of a plurality of autonomous sensor units spatially distributed within the area to be monitored; each sensor unit is configured to monitor environmental conditions of a respective portion of the area, such as temperature, sound, vibration, pressure, motion or pollutants concentration.

The SN is configured to forward the data collected by the sensor units to a remote server, possibly by means of a gateway, through an external network—such as the Internet—for being accessed by an end user.

A Wireless Sensor Network (WSN) is a particular SN wherein the sensor units are connected to each other—and to the gateway as well—by means of a wireless link.

A system of this type may be advantageously implemented with relatively inexpensive sensor units, provided with the bare minimum equipment to operate (such as the sensor itself, an energy source and/or an energy scavenging system, a simple microcontroller and a transceiver), on condition that the heaviest computational processes are delegated to a base unit, for example remotely connected to the WSN through the gateway.

A further known system implementing an area monitoring service provides for the use of one or more mobile sensor units, adapted to travel within the area to be monitored. For example, the mobile sensor units may be self-propelled automatically operated machines—from now on referred to as "robot"—equipped with proper sensors. Such robots may be configured to automatically patrol the area to be monitored, e.g., following a predetermined or dynamically calculated patrol path, for sequentially monitoring portions of the whole area with the sensors during the movement along the patrol path. In this way, instead of having to install a high number of static sensor units to cover the whole area to be monitored, a lower number of mobile robots equipped with sensors may be sufficient.

The Chinese patent application CN101468664 relates to small-sized caterpillar type inspection robot system for dangerous cable tunnel environment, which comprises a movable platform, an upper cover, a gas sensor box, a data transmission antenna, an image transmission antenna, a thermal camera tripod head, an ultrasonic sensor, a wireless monitoring device, a control box, a control unit and an operation panel, wherein the movable platform comprises a front guide belt wheel, a locking bolt, a swinging arm, a first tension bolt, a front load-bearing wheel, a second tension screw, a middle guide wheel, a caterpillar, a rear load-bearing wheel, a worm speed reducer, a swinging arm motor and a driving motor. The system overcomes the drawbacks of the prior cable tunnel inspection technology, avoids dangerous factors caused by manual inspection, simplifies the robot mechanism and provides a simple, high-efficiency and reliable mechanism for cable tunnel inspection.

The US patent US 2009/023449 discloses systems, methods, and user interfaces for controlling a robot. An environment map and a robot designator are presented to a user. The user may place, move, and modify task designators on the environment map. The task designators indicate a position in the environment map and indicate a task for the robot to achieve. A control intermediary links task designators with robot instructions issued to the robot. The control intermediary analyzes a relative position between the task designators and the robot. The control intermediary uses the analysis to determine a task-oriented autonomy level for the robot and communicates target achievement information to the robot. The target achievement information may include instructions for directly guiding the robot if the autonomy level indicates low robot initiative and may include instructions for directing the robot to determine a robot plan for achieving the task if the autonomy level indicates high robot initiative.

The US patent US 2008/0009969 relates to methods and system for controlling a plurality of robots through a single user interface. The user interface includes at least one robot display window for each of the plurality of robots with the at least one robot display window illustrating one or more conditions of the respective one of the plurality of robots. The user interface further includes at least one robot control window for each of the plurality of robots with the at least one robot control window configured to receive one or more commands for sending to the respective one of the plurality of robots. The user interface further includes a multi-robot common window comprised of information received from each of the plurality of robots.

SUMMARY OF THE INVENTION

The Applicant has found that the abovementioned systems known in the art implementing an area monitoring service are affected by several drawbacks.

Specifically, even if a monitoring system arranged as a sensor network may be advantageously implemented with relatively inexpensive sensor units, if the environmental condition(s) object of the monitoring system requires to be monitored with high precision, more sophisticated (and more expensive) sensor units should be required, which are eager of power. Furthermore, in order to efficiently cover the whole area to be monitored, without leaving un-monitored portions thereof, the number of sensor units should be kept as higher as possible, strongly increasing the installation and management costs.

The known solutions providing for the use of robots equipped with sensors are affected by drawbacks, too. Specifically, in order to be capable of autonomously facing any unforeseen issue, such as the sudden appearance of an obstacle blocking the planned patrol path, a robot should be provided with sufficiently evolved decisional resources. Since a robot of this type is quite expensive, the number of robots configured to operate in a same area to be monitored should be kept as small as possible. However, if the area to be monitored is broad, a small number of robots might not be sufficient for an efficient service.

The Applicant has tackled the problem of how to improve the already existing systems that implement an area monitor service. Specifically, the Applicant has tackled the problem of how to improve the energy efficiency of the system, as well as to reduce the installation costs and the management costs of the system, providing at the same time a reliable service capable of monitoring the area with a sufficiently high accuracy.

An aspect of the present invention relates to a monitoring system for monitoring an environmental condition of an area through the measurement of a corresponding environmental quantity. The system comprises a static monitoring section comprising a plurality of static sensor units; each static sensor unit is configured to collect first measure data relating to the environmental quantity in a respective portion of the area according to first predetermined scheduled routines. The system further includes a mobile monitoring section comprising at least one robot; each one of said at least one robot is configured to move itself within the area and is configured to collect second measure data relating to the environmental quantity in a portion of the area surrounding the at least one robot itself according to second predetermined scheduled routines. The system still further includes a central unit in communication relationships with the static sensor units and the at least one robot for receiving the first measure data and the second measure data and assessing the environmental condition of the area based on at least one between the received first and second measure data. The central unit is configured to perform at least one between:
  conditioned to the assessing of an anomalous environmental condition from first measure data collected by at least one static sensor unit, commanding at least one robot to operate according to anomaly routines under the control of the central unit, and
  conditioned to the assessing of an anomalous environmental condition from second measure data collected by at least one robot, commanding at least one static sensor unit to operate according to anomaly routines under the control of the central unit.

Thanks to the cooperation between sensors equipped on static sensor units and sensors equipped on mobile robots managed by a central unit, the proposed monitoring system is more flexible and efficient compared to the known monitoring systems provided with an extensive coverage of static sensor units only. Moreover, the proposed monitoring system is less expensive compared to the known monitoring systems based exclusively on robots, since it is possible to use a very few number of robots (e.g., only one); indeed, the presence of the central unit guarantees that such few robots are driven toward the locations of the area wherein the monitoring is most required.

According to an embodiment of the present invention, each robot is configured to autonomously wander within the area when operating according to the second predetermined scheduled routines.

According to an embodiment of the present invention, each static sensor unit is equipped with sensors configured to collect the first measure data with a first sampling rate when operating according to the first predetermined scheduled routines, and each robot is equipped with sensors configured to collect the second measure data with a second sampling rate when operating according to the second predetermined scheduled routines.

Preferably, the sensors of at least one static sensor unit are configured to collect the first measure data with a third sampling rate higher than the first sampling rate when operating according to the anomaly routines, and/or the sensors of at least one robot are configured to collect the second measure data with a fourth sampling rate higher than the second sampling rate when operating according to the anomaly routines.

Advantageously, each robot is configured to being driven within the area by the central unit when operating according to the anomaly routines.

According to an embodiment of the present invention, conditioned to the assessing of an anomalous environmental condition, the central unit is configured to drive at least one robot toward a portion of the area wherein such anomalous environmental condition has been assessed and then is instructed not to leave that portion of the area, autonomously investigating the origin of the anomalous environmental condition, until the environmental condition changes or a given amount of time is expired.

The environmental quantity may be a selected one among the set of quantities including temperature, sound, vibration, pressure, motion and pollutants concentration.

According to an embodiment of the present invention, each static sensor unit is equipped with temperature sensors, and each robot is equipped with a thermographic camera.

Another aspect of the present invention provides for a corresponding method for monitoring an environmental condition of an area through the measurement of a corresponding environmental quantity. The method comprises collecting first measure data relating to the environmental quantity through a plurality of static sensor units according to first predetermined scheduled routines and collecting second measure data relating to the environmental quantity through at least one robot configured to move itself within the area according to second predetermined scheduled routines. The method further comprises, at a central unit, receiving the first measure data and the second measure data, and assessing the environmental condition of the area based on at least one between the received first and second measure data. The method still further comprises performing at least one among:
  conditioned to the assessing of an anomalous environmental condition from first measure data collected by at least one static sensor unit, commanding at least one robot to operate according to anomaly routines under the control of central unit, and
  conditioned to the assessing of an anomalous environmental condition from second measure data collected by at least one robot, commanding at least one static sensor unit to operate according to anomaly routines under the control of the central unit.

According to an embodiment of the present invention, the method further comprises at the static sensor units, collecting the first measure data with a first sampling rate when operating according to the first predetermined scheduled routines, and at the at least one robot, collecting the second measure data with a second measure data with a second sampling rate when operating according to the second predetermined scheduled routines.

According to a further embodiment of the present invention, the static sensor units collect the first measure data with a third sampling rate higher than the first sampling rate when operating according to the anomaly routines.

According to a still further embodiment of the present invention, the at least one robot collects the second measure data with a fourth sampling rate higher than the second sampling rate when operating according to the anomaly routines.

Advantageously, the central unit, conditioned to the assessing of an anomalous environmental condition, drives at least one robot toward a portion of the area wherein such anomalous environmental condition has been assessed.

BRIEF DESCRIPTION OF THE DRAWINGS

These and other features and advantages of the present invention will be made evident by the following description of some exemplary and non-limitative embodiments thereof, to be read in conjunction with the attached drawings, wherein.

DETAILED DESCRIPTION OF EXEMPLARY EMBODIMENTS OF THE INVENTION

Figure 1:
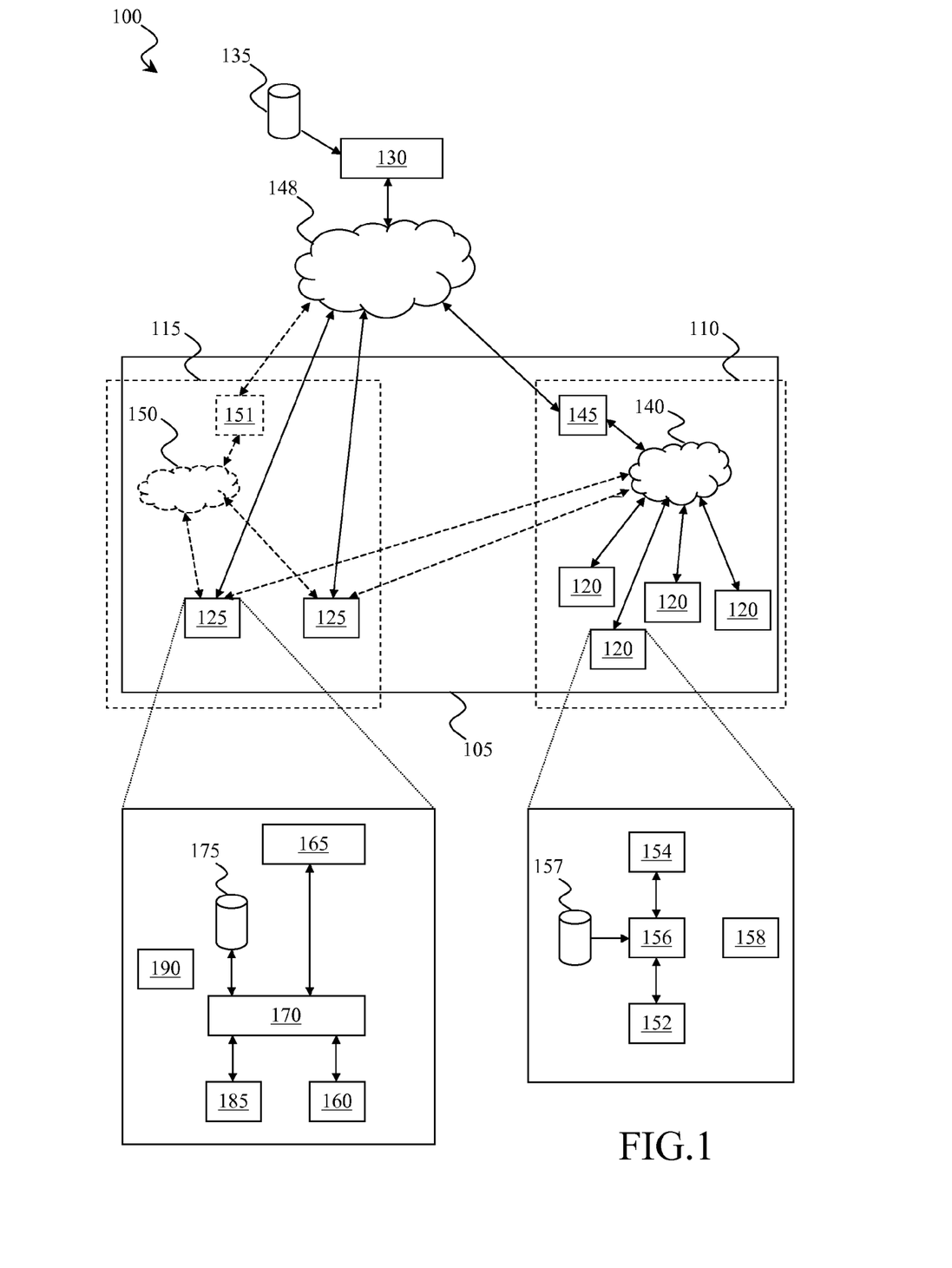
FIG. 1 depicts an area monitoring system according to an embodiment of the present invention.

With reference to the drawings, FIG. 1 illustrates in terms of functional blocks an area monitoring system 100 according to an embodiment of the present invention. The area monitoring system 100 is configured to monitor an environmental condition of an area 105 through the measurement of a corresponding environmental quantity. For example, the area monitoring system 100 may implement a "green computing" service for the monitoring of temperature within a server farm; in this case, the area 105 to be monitored by the area monitoring system 100 is the place wherein the servers forming the server farm are physically located.

According to an embodiment of the present invention, the area monitoring system 100 includes two main sections, and specifically a static section, identified in the figure with the reference 110, and a mobile section, identified in the figure with the reference 115. The static section 110 comprises a plurality of static sensor units 120 spatially arranged within the area 105, while the mobile section 115 comprises at least one robot 125 configured to autonomously patrol the area 105.

The static section 110 and the mobile section 115 of the area monitoring system 100 are managed by a central unit 130, for example a server supporting proper control and surveillance applications, schematically identified in figure with the reference 135. As will be described in greater detail in the following of the description, according to an embodiment of the present invention the static section 110 and the mobile section 115 jointly operate under the mediation of the central unit 130; in other words, the central unit 130 acts as a middleware.

The area monitoring system 100 according to the embodiment of the invention illustrated in FIG. 1 provides for a constant monitoring of the area 105 through the static sensor units 120; the static sensor units 120 are configured to measure an environmental quantity—in the example at issue, the temperature—of a respective portion of the area 105.

According to an embodiment of the present invention, the static sensor units 120 are configured to transmit (and receive) data to (from) the central unit 130 in real time. More particularly, the static sensor units 120 are connected to a local sensor network 140, for example of the wireless type, which is in turn coupled to an access control unit 145. The measure data generated by the various static sensor units 120 during the monitoring of the area 105 are sent through the local sensor network 140 for being collected by the access control unit 145, which forwards them to the central unit 130. Similarly, the central unit 130 is configured to forward commands to the static sensor units 120 by sending them—through the access control unit 145—on the local sensor network 140.

The central unit 130 may be directly installed within (or in the close proximity of) the area 105 to be monitored, or may be located in a location that is remote with respect to the area 105. In the former case, the central unit 130 is directly connected to the access control unit 145. If instead the central unit 130 is remote, the central unit 130 and the local sensor network 140 are coupled by means of an external network 148, such as the Internet. In case the transmission/reception protocol used in the local sensor network 140 (e.g., a local radio protocol, such as the ZigBee protocol) is different than the one used in the external network 148 (e.g., the Internet Protocol (IP), the interfacing between such two different protocols is carried out by the access control unit 145. In both cases, the access control unit 145 operates as a gateway.

According to an embodiment of the present invention, the control and surveillance applications 135 used by the central unit 130 for operating the area monitoring system 100 are locally installed in the central unit 130 itself; according to a further embodiment of the present invention (non illustrated) the control and surveillance applications 135 are instead remotely provided to the central unit 130 via the external network 148.

According to an embodiment of the present invention, each static sensor unit 120 comprises:

At least a sensor 152 for monitoring the environmental condition of a respective portion of the area 105 through the generation of measure data relating to a corresponding environmental quantity; in the example considered, said sensor is a temperature sensor, the environmental quantity is the temperature, and said measure data are temperature values.

A transceiver unit 154 for transmitting measure data collected by the sensor 152 to the central unit 130 and for receiving commands sent by the central unit 130; in the example considered, the transceiver unit includes a wireless interface with an internal antenna or a connection to an external antenna.

A sensor central unit 156 configured to drive the other sections of the static sensor unit 120 under the control of a sensor local application 157, so that, in absence of external commands, the static sensor unit 120 operates following predetermined scheduled routines.

An energy source 158, such as a battery and/or an energy scavenging system, for the supplying of the sensor 152, the transceiver unit 154 and the sensor central unit 156.

The sensor local application 157 is preferably installed in the static sensor unit 120 itself, for example in the form of program instructions stored in a local memory unit; however, similar considerations apply if such application is remote, for example provided to the static sensor unit 120 through the local sensor network 140.

According to an embodiment of the present invention, in addition to the monitoring through the static sensor units 120, the area monitoring system 100 provides at the same time for a monitoring of the area 105 through sensors equipped on the at least one robot 125. Like the static sensor units 120, the robots 125 as well are configured to transmit (and receive) data to (from) the central unit 130 in real time.

According to an embodiment of the present invention, the measure data generated by the robots 125 during the monitoring of the area 105 are sent to the central unit 130 directly through the external network 148. Similarly, the central unit 130 forwards commands to the static sensor units 120 by sending them directly through the external network 148.

According to a further embodiment of the present invention, the robots 125 and the central unit 130 exchange data with a network configuration similar to that employed for the static sensor units 120, with the robots 125 that are connected to a local robot network 150, for example of the wireless type, which is in turn coupled to a corresponding further access control unit 151.

According to a still further embodiment of the present invention, the robots 125 are instead interfaced with the local sensor network 140 used by the static sensor unit 120.

According to an embodiment of the present invention, each robot 125 comprises:

At least a sensor 160 for monitoring the environmental condition of the portion of the area 105 surrounding the robot 125 through the generation of measure data relating to a corresponding environmental quantity (preferably more sophisticated and more accurate than the sensors 152 equipped on the static sensor units 120); in the example considered, said sensor is a thermographic camera, the environmental quantity is the temperature, and said measure data are thermal images.

A transceiver unit 165 equipped with an antenna for transmitting measure data collected by the sensor 160 to the central unit 130 and for receiving commands sent by the central unit 130; for example, in case the robot 125 is configured to directly exchange data through the external network 148 the transceiver unit is equipped with a Subscriber Identity Module (SIM), otherwise it includes a wireless interface.

A robot central unit 170 configured to drive the other sections of the robot 125 under the control of a robot local application 175, so that, in absence of external commands, the robot 125 operates following predetermined scheduled routines; the robot central unit 170 is further configured to receive commands from the central unit 130 and accordingly drive the robot 125 to perform special routines that are not contemplated by the robot local application 175.

A locomotion unit 185 configured to provide the robot 125 with moving capabilities, such as for example wheels and/or caterpillars adapted to be moved by a corresponding motor (not shown).

An energy source 190, such as a battery and/or an energy scavenging system, for the supplying of the other sections of the robot 125.

Like the sensor local application 157, the robot local application 175 as well is preferably installed in the robot 125 itself, for example in the form of program instructions stored in a local memory unit; however, similar considerations apply if such application is remote, for example provided to the robot 125 through the external network 148.

According to an embodiment of the present invention, the central unit 130 is configured to modify in real time the behavior of the static section 110 and of the mobile section 115, so as to improve the area monitoring service based on the actual condition of the area 105.

Specifically, until the area 105 is assessed to be in a standard environmental condition (from now on, simply "standard condition"), the area monitoring system 100 operates in a corresponding standard status, with the static sensor units 120 and the robots 125 that operate following respective predetermined scheduled routines.

As soon as a static sensor unit 120 or a robot 125 assesses an anomaly or a deviation from the standard condition that is susceptible of a thorough analysis, the central unit 130 takes the control of the operation for better investigating the causes of such anomaly. For this purpose, according to an embodiment of the present invention at least one robot 125 is instructed by the central unit 130 to proceed toward the portion of the area 105 wherein such anomaly has been detected, and remain confined within such portion for collecting more detailed measure data. Moreover, the central unit 130 may additionally instruct the sensors (both those on the static sensor units 120 and those on the robots 125) to collect measure data with a sampling rate higher than that used in the standard status. Moreover, the central unit 130 may update a suitable anomaly log for keeping track of any anomaly event occurred in the area 105.

If the condition get worse (i.e., if the deviation from the standard condition further increases), the central unit 130 may additionally issue alarm signals, through real time communications (e.g., an email or an SMS) and/or by updating an alarm log, for signaling the occurrence of such anomalous condition to an user of the area monitoring system 100.

Figure 2:
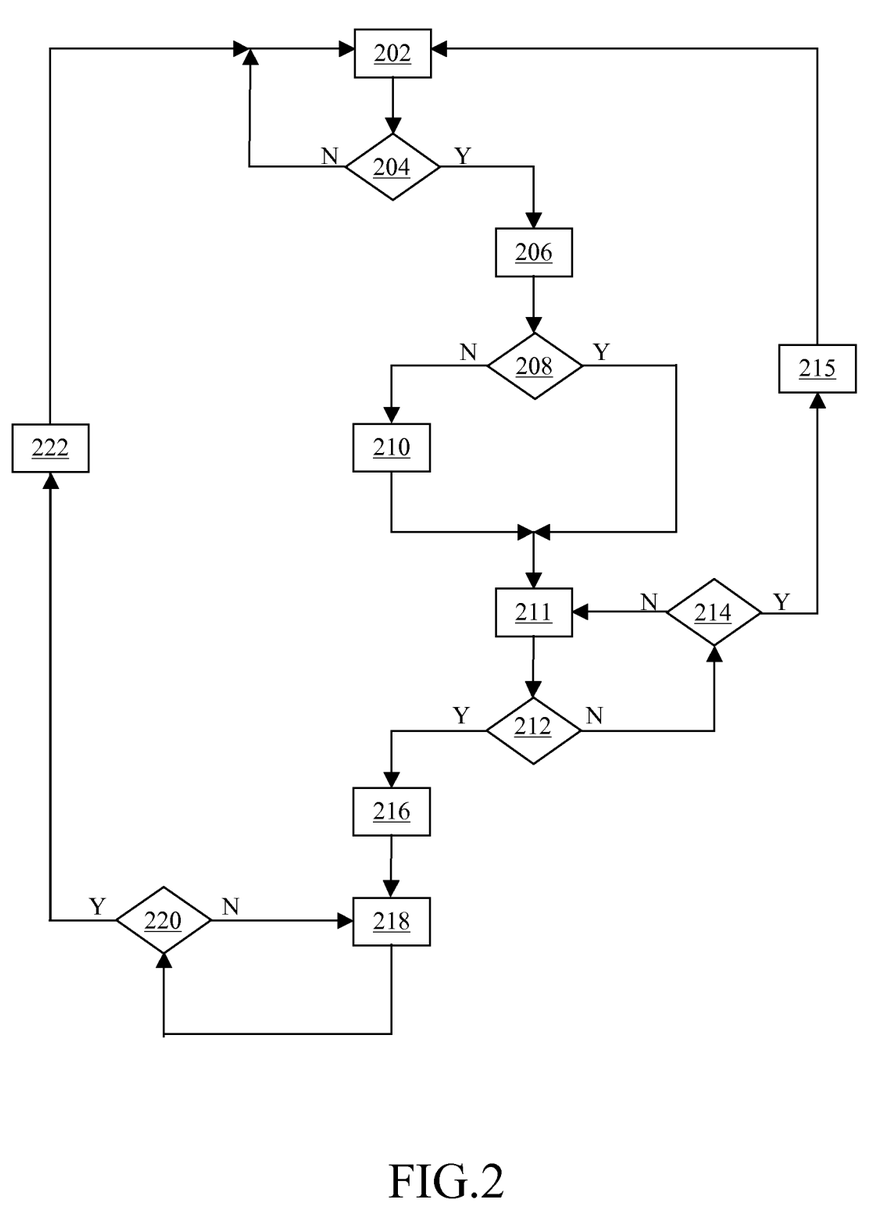
FIG. 2 is a flow chart illustrating operations carried out by the area monitoring system of FIG. 1.

In order to illustrate in greater detail how the area monitoring system 100 operates according to an embodiment of the present invention, reference is now made to the flow chart illustrated in FIG. 2.

When the area monitoring system 100 is in a "standard status" (block 202), the sensors 152 of the static sensor units 120 collect measure data relating to the monitored environmental quantity with a sample frequency sf1, while the sensors 160 of the robots 125 collect measure data relating to the same monitored environmental quantity with a sample frequency rf1.

In this situation, the robots 125 autonomously operate following respective predetermined scheduled routines, under the control of the robot local application 175. For example, depending on the robot local application 175, each robot 125 may be driven in such a way to follow a predetermined patrol path or wander within the area 105 to be monitored, automatically avoiding any obstacle.

The measure data are sent to the central unit 130 as soon as they are collected by the static sensor units 120 and the robots 125. According to an embodiment of the present invention, the measure data collected by the static sensor units 120 are sent to the access control unit 145 through the local sensor network 140, which forward them to the central unit 130 through the external network 148, while the measure data collected by the robots 125 are sent to the central unit 130 directly through the external network 148, or through the access control unit 151.

The measure data are received by the central unit 130, which checks whether their values fall within prescribed standard condition ranges or not. As long as the measured data are comprised within the standard condition range, the area 105 is considered to be in the standard condition, and the area monitoring system 100 is maintained in the standard status (exit branch "N" of block 204, returning back to block 202).

Figure 3A:
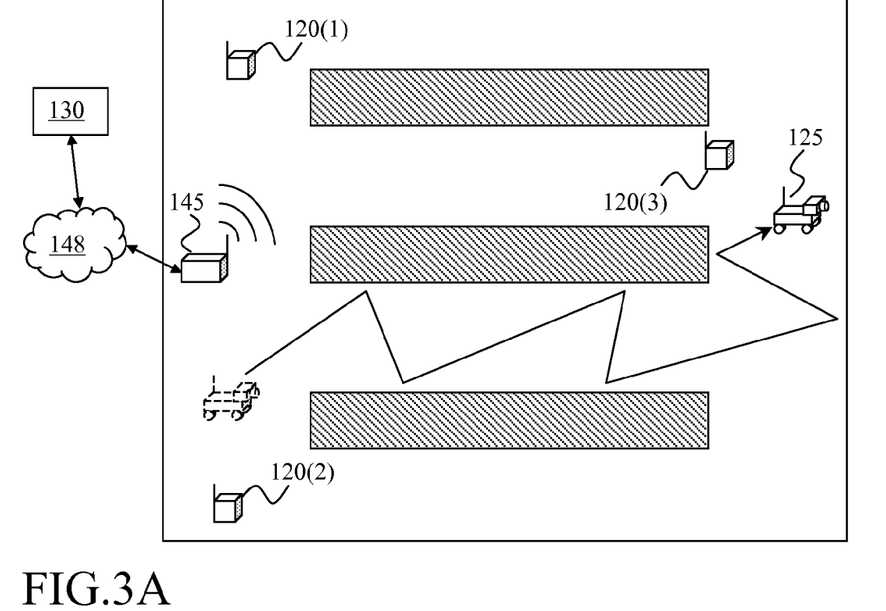
FIG. 3A illustrates an area monitoring system according to an embodiment of the present invention when operating in a standard status.

FIG. 3A illustrates an exemplary area monitoring system when operating in the standard status. In this example, the static portion of the system includes three static sensor units 120(1), 120(2) and 120(3), and the mobile portion includes a single robot 125, which wanders autonomously between the area 105 to be monitored.

Returning to FIG. 2, as soon as the measured data received by the central unit 130 from at least one static sensor unit 120 or robot 125 fall outside the corresponding standard condition range, an anomaly is detected, and the status of the area monitor system 100 is switched by the central unit 130 to an "anomaly status" (exit branch "Y" of block 204, proceeding to block 206).

In the anomaly status, the central unit 130 starts an anomaly timer ant, and commands the static sensor units 120 and the robots 125 to operate according to new anomaly routines (different than the predetermined scheduled ones) under the control of the central unit 130 itself.

Specifically, according to an embodiment of the present invention the anomaly routines set by the central unit 130 provide for increasing the sample frequencies of (at least some of) the static sensor units 120 and the robots 125. More in particular, in the anomaly status the sensors 152 of (at least a subset of) the static sensor units 120 collect measure data with a sample frequency sf2>sf1, and the sensors 160 of (at least one of) the robots 125 collect measure data with a sample frequency rf2>rf1.

Moreover, the central unit 130 is capable of determining in which portion of the area 105 the anomaly has occurred by identifying the source of the measured data that have fallen outside the prescribed standard ranges. For example, if such measured data originate from a specific static sensor unit 120, the anomaly is presumably caused by something that is occurring in a portion—from now on referred to as "anomaly area"—of the area 105 that is close to said specific static sensor unit 120. If there are not robots 125 within such anomaly area (exit branch "N" of block 208), the anomaly routines set by the central unit 130 provides for commanding at least one robot 125 to proceed toward the anomaly area (block 210). Once said at least one robot 125 has reached the anomaly area, or in case a robot 125 was already inside the anomaly area when the anomaly has been detected (exit branch "Y" of block 208), the anomaly routine set by the central unit 130 provides for driving such at least one robot 125 in such a way to wander confined within such anomaly area (block 211). Thanks to the presence of at least one robot 125 (which is preferably equipped with sensors that are more sophisticated and more accurate than the sensors of the static sensor units 120) within the anomaly area, and thanks to the increased sample frequencies sf2, rf2, during the anomaly status the central unit 130 receives a greater amount of (better) data regarding the anomaly area, so as to ease a following analysis of the situation. Moreover, the central unit 130 may record the occurrence of the anomaly event by updating a corresponding anomaly log.

Figure 3B:
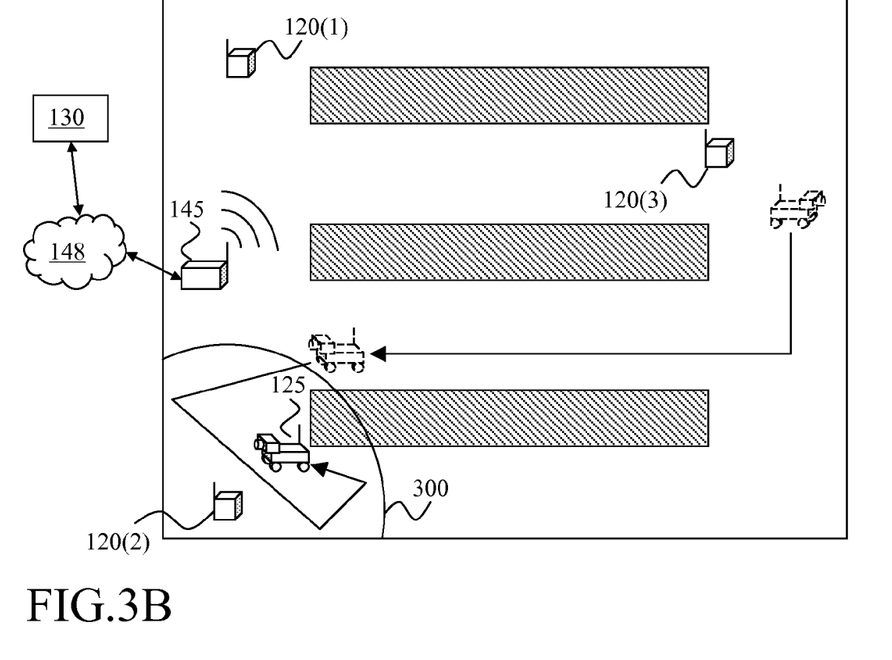
FIG. 3B illustrates the area monitoring system of FIG. 3A when operating in an anomaly status.

FIG. 3B illustrates the exemplary area monitoring system of FIG. 3A when operating in the anomaly status, further to the occurrence of an anomaly condition. In the example at issue, the measure data that have fallen outside the standard condition range have been generated by the static sensor unit 120(2). In this case, the central unit 130 defines within the area 105 a corresponding anomaly area 300 around such static sensor unit 120(2). For example, the anomaly area 300 is a circular area having a center corresponding to the location of the static sensor unit 120(2) and a radius R.

Returning to FIG. 2, the anomaly status is maintained by the central unit 130 until the anomaly timer ant expires, or a worse anomaly is detected.

Specifically, if the anomaly previously detected does not get worse (exit branch "N" of block 212, going to block 214), in the sense that the measured data collected by the sensor unit(s) 120 and/or the robot(s) 125 within the anomaly area do not sensibly increase their distances from the corresponding standard condition range, the central unit 130 checks the value assumed by the anomaly timer ant. If the anomaly timer ant is still lower than (or equal to) a first threshold th1, the anomaly status is maintained (exit branch "N" of block 214, returning to block 211); if instead the anomaly timer ant exceeds the first threshold th1, the central unit 130 switches back the status of the area monitor system 100 to the standard status (exit branch "Y" of block 214, returning to block 202), with the central unit 130 that resets the anomaly timer ant, and sets the static sensor units 120 and the robots 125 to operate again according to the respective predetermined scheduled routines. Specifically, the central unit 130 commands the static sensor units 120 and the robots 125 to decrease their sample frequencies to sf1 and rf1, respectively, and allows the robot(s) 125 previously confined in the anomaly area to freely wander within the entire area 105. According to an embodiment of the present invention, before switching back the status of the area monitor system 100 to the standard status, the central unit 130 sets an anomaly dismiss timer adt associated to the previously detected anomaly (block 215). During the subsequent standard status, and as long as such anomaly dismiss timer adt is lower than a predefined threshold, the central unit 130 is configured to ignore the presence of the anomaly associated to the counter, in such a way to allow the detection of further, different, anomalies.

Conversely, if the anomaly previously detected gets worse, in the sense that the measured data collected by the sensor unit(s) 120 and/or the robot(s) 125 within the anomaly area have increased their distances from the corresponding standard condition range of an extent higher than a corresponding alarm threshold, the status of the area monitor system 100 is switched by the central unit 130 to an "alarm status" (exit branch "Y" of block 212, going to block 216).

In the alarm status (block 216), the central unit 130 starts an alarm timer alt, and commands the static sensor units 120 and the robots 125 to operate according to new alarm routines (different than the anomaly routines) under the control of the central unit 130 itself.

Specifically, according to an embodiment of the present invention the alarm routines set by the central unit 130 provide for driving (at least some of) the static sensor units 120 and the robots 125 to further increase their sample frequencies. Specifically, in the alarm status the sensors 152 of (at least a subset of) the static sensor units 120 collect measure data with a sample frequency sf3>sf2, and the sensors 160 of (at least one of) the robots 125 collect measure data with a sample frequency rf3>rf2. During the alarm status, the central unit 130 issues alarm signals, for example through real time communications (e.g., email or SMS) and/or by updating an alarm log, for signaling the occurrence of such alarm to an user of the area monitoring system 100.

Moreover, according to an embodiment of the present invention, during the alarm status the alarm routines set by the central unit 130 provides for further reducing the extension of the anomaly area, e.g., by reducing the radius R thereof (block 218).

The alarm status is maintained by the central unit 130 until the alarm timer alt expires. Specifically, as long as the alarm timer alt is lower than (or equal to) a second threshold th2, the alarm status is maintained (exit branch "N" of block 220, returning to block 218); if instead the alarm timer alt exceeds the second threshold th2, the central unit 130 switches back the status of the area monitor system 100 to the standard status (exit branch "Y" of block 220, returning to block 202), with the central unit 130 that resets the alarm timer alt, and sets the static sensor units 120 and the robots 125 to operate again according to the respective predetermined scheduled routines. Specifically, the static sensor units 120 and the robots 125 are driven to decrease their sample frequencies to sf1 and rf1, respectively, and the robot(s) 125 previously confined in the reduced anomaly area are allowed to freely wander within the entire area 105. According to an embodiment of the present invention, before switching back the status of the area monitor system 100 to the standard status, the central unit 130 sets an alarm dismiss timer aldt associated to the previously detected worsened anomaly (block 222). During the subsequent standard status, and as long as such alarm dismiss timer aldt is lower than a predefined threshold, the central unit 130 is configured to ignore the presence of the anomaly associated to the counter, in such a way to allow the detection of further anomalies.

The synergic cooperation between sensors equipped on static sensor units and sensors equipped on mobile robots managed by a central unit is more flexible and efficient compared to the known monitoring systems provided with an extensive coverage of static sensor units only. Moreover, with the proposed solution it is possible to reduce the global cost of the system by using a very few number of robots (e.g., only one), since the presence of the central unit guarantees that such robots are driven toward the locations of the area wherein the monitoring is most required. Moreover, the resulting system has an improved energy efficiency, it can be installed with ease and require a very low management effort.

The previous description presents and discusses in detail several embodiments of the present invention; nevertheless, several changes to the described embodiments, as well as different invention embodiments are possible, without departing from the scope defined by the appended claims.

The concepts of the present invention are also applicable in case the at least one robot is kept in a steady state—wherein the robot does not move—during the standard status, and it is activated by the central unit only when the system enters in the anomaly status, for being driven toward the portion of the area wherein the anomaly has been detected.

Moreover, similar considerations apply if the cooperation between static sensor units and mobile robots managed by the central unit provides for, once the occurrence of an anomaly has been detected by a robot, driving only the static sensor units with the anomaly routines (e.g., for increasing the sample frequencies thereof), leaving the robot to operate according to the predetermined scheduled routines.

Even if reference has been made to an area monitoring system implementing a service for the monitoring of temperature, similar considerations apply if each sensor (both in the static sensor units and in the robots) is configured to monitor different environmental conditions through the measurement of different environmental quantities, such as sound, vibration, pressure, motion, pollutants concentration and the like.

The invention claimed is:

1. A monitoring system for monitoring an environmental condition of an area through the measurement of a corresponding environmental quantity, the system comprising:
a static monitoring section comprising a plurality of static sensor units, each static sensor unit being configured to collect first measure data relating to the environmental quantity in a respective portion of the area according to first predetermined scheduled routines;
a mobile monitoring section comprising at least one robot, each one of said at least one robot being configured to move itself within the area and being configured to collect second measure data relating to the environmental quantity in a portion of the area surrounding the at least one robot itself according to second predetermined scheduled routines, and
a central unit in communication relationships with the static sensor units and the at least one robot for receiving the first measure data and the second measure data and assessing the environmental condition of the area based on at least one between the received first and second measure data, the central unit being configured to perform at least one between:
conditioned to the assessing of an anomalous environmental condition from first measure data collected by at least one static sensor unit, commanding at least one robot to operate according to anomaly routines under the control of the central unit, and
conditioned to the assessing of an anomalous environmental condition from second measure data collected by at least one robot, commanding at least one static sensor unit to operate according to anomaly routines under the control of the central unit.

2. The monitoring system of claim 1, wherein each robot is configured to autonomously wander within the area when operating according to the second predetermined scheduled routines.

3. The monitoring system of claim 1, wherein:
each static sensor unit is equipped with sensors configured to collect the first measure data with a first sampling rate when operating according to the first predetermined scheduled routines, and
each robot is equipped with sensors configured to collect the second measure data with a second sampling rate when operating according to the second predetermined scheduled routines.

4. The monitoring system according to claim 3, wherein the sensors of at least one static sensor unit are configured to collect the first measure data with a third sampling rate higher than the first sampling rate when operating according to the anomaly routines.

5. The monitoring system according to claim 3, wherein the sensors of at least one robot are configured to collect the second measure data with a fourth sampling rate higher than the second sampling rate when operating according to the anomaly routines.

6. The monitoring system of claim 1, wherein each robot is configured to being driven within the area by the central unit when operating according to the anomaly routines.

7. The monitoring system of claim 6, wherein, conditioned to the assessing of an anomalous environmental condition, the central unit is configured to drive at least one robot toward a portion of the area wherein such anomalous environmental condition has been assessed.

8. The monitoring system of claim 7, wherein, conditioned to the assessing of said anomalous environmental condition, the central unit is further configured to drive said at least one robot in such a way said at least one robot remains confined within said portion of the area wherein such anomalous environmental condition has been assessed.

9. The monitoring system of claim 1, wherein such environmental quantity is a selected one among the set of quantities including temperature, sound, vibration, pressure, motion and pollutants concentration.

10. The monitoring system of claim 4, wherein:
- each static sensor unit is equipped with temperature sensors, and
- each robot is equipped with a thermographic camera.

* * * * *